(12) United States Patent
Castellanos

(10) Patent No.: US 8,586,296 B2
(45) Date of Patent: Nov. 19, 2013

(54) METHOD TO IDENTIFY AND PREDICT DISEASE PROGRESSION OF HUMAN PAPILLOMA VIRUS-INFECTED LESIONS

(75) Inventor: Mario R Castellanos, Brooklyn, NY (US)

(73) Assignees: Staten Island University Hospital, Staten Island, NY (US); The Feinstein Institute for Medical Research, Manhasset, NY (US)

( * ) Notice: Subject to any disclaimer, the term of this patent is extended or adjusted under 35 U.S.C. 154(b) by 358 days.

(21) Appl. No.: 12/972,775

(22) Filed: Dec. 20, 2010

(65) Prior Publication Data

US 2011/0091867 A1    Apr. 21, 2011

Related U.S. Application Data

(63) Continuation-in-part of application No. PCT/US2009/049539, filed on Jul. 2, 2009.

(60) Provisional application No. 61/078,050, filed on Jul. 3, 2008.

(51) Int. Cl.
*C12Q 1/70*     (2006.01)
*C07H 23/00*    (2006.01)

(52) U.S. Cl.
USPC ............................................. 435/5; 536/23.1

(58) Field of Classification Search
None
See application file for complete search history.

(56) References Cited

U.S. PATENT DOCUMENTS

| 2003/0175770 A1 | 9/2003 | Gocke et al. |
| 2003/0211491 A1 | 11/2003 | Mai |
| 2004/0203004 A1 | 10/2004 | Bernard et al. |
| 2006/0216706 A1 | 9/2006 | Tang et al. |
| 2007/0238100 A1* | 10/2007 | McGlennen et al. ............. 435/6 |

OTHER PUBLICATIONS

Durst et al. (Journal of General Virology, 1985, vol. 66, p. 1515-1522).*
Lazo (European Journal of Biochemistry, 1987, vol. 165, p. 393-401).*
PCT International Search Report, Aug. 27, 2009, for Staten Island University Hospital et al., Int'l App'l No. PCT/US2009/049539, filed Jul. 2, 2009.
PCT Written Opinion of the International Searching Authority, Aug. 27, 2009, for Staten Island University Hospital et al., Int'l App'l No. PCT/US2009/049539, filed Jul. 2, 2009.
PCT Notification Concerning Transmittal of International Preliminary Report on Patentability (IPRP), Jan. 13, 2011, for Staten Island University Hospital et al., Int'l App'l No. PCT/US2009/049539, filed Jul. 2, 2009.

* cited by examiner

*Primary Examiner* — Agnieszka Boesen
(74) *Attorney, Agent, or Firm* — Law Offices of Albert Wai-Kit Chan, PLLC

(57) ABSTRACT

The present invention provides a method for distinguishing benign human papilloma virus (HPV)-infected tissue from HPV-related lesions that have undergone malignant transformation. In one embodiment, the invention comprises a simple histochemical staining method and details a novel process for examining HPV-infected cells by determining susceptibility to enzymatic DNA digestion. Residual virion-associated DNA is seen only in benign HPV-infected lesions, while absence of residual DNA is seen with malignant transformation. In another embodiment, the invention comprises immunohistochemical assay methods for examining HPV-infected cells, utilizing antibodies to HPV L1 proteins. These methods can be used to predict biologic behavior of HPV-infected lesions. The invention can improve current cervical cancer screening programs, and improve clinical management of patients by defining malignant potential of HPV-infected tissue more accurately.

8 Claims, 4 Drawing Sheets

Figure 1A. H & E stain Conyloma
Figure 1B. DNase stain Condyloma
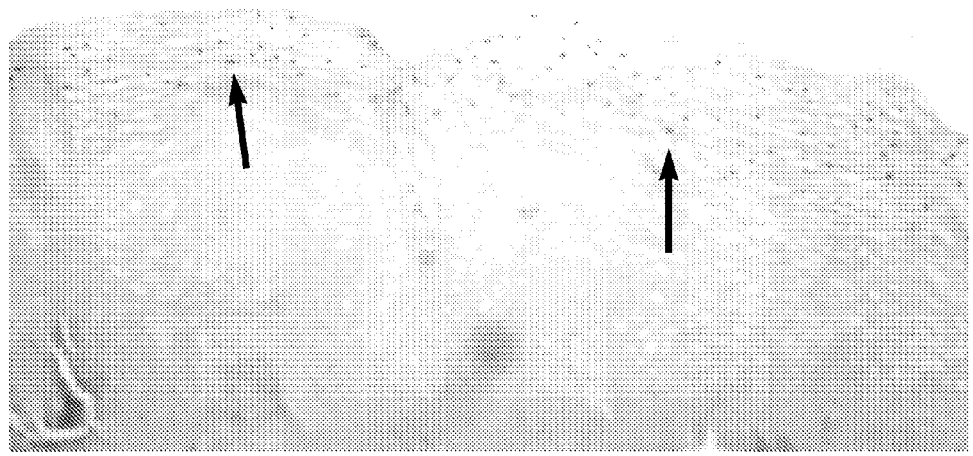

Figure 2A. H & E stain CIN III
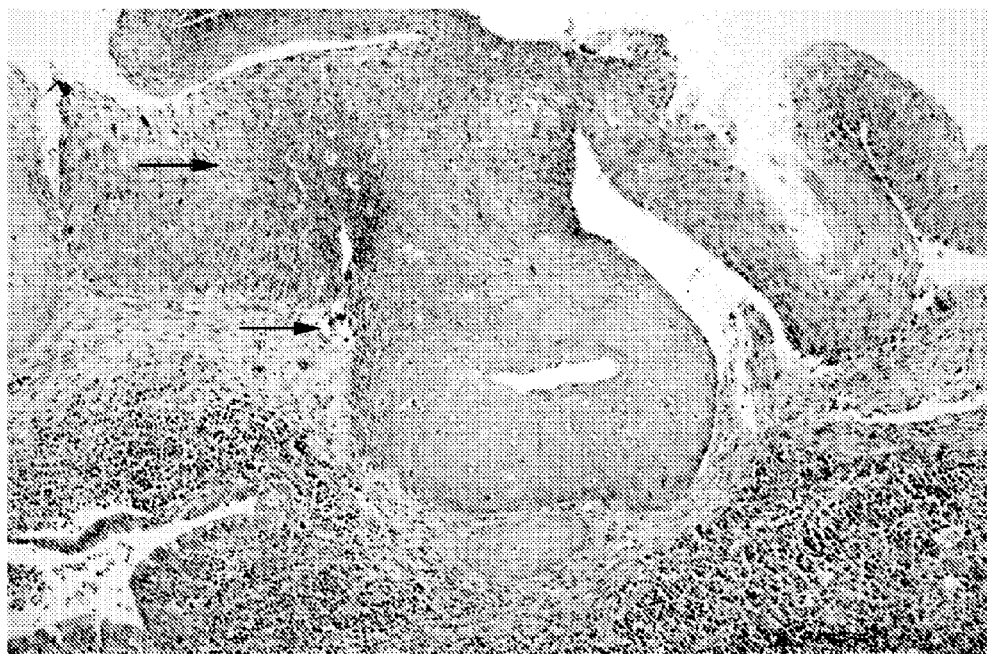
Figure 2B. DNAase stain CIN III
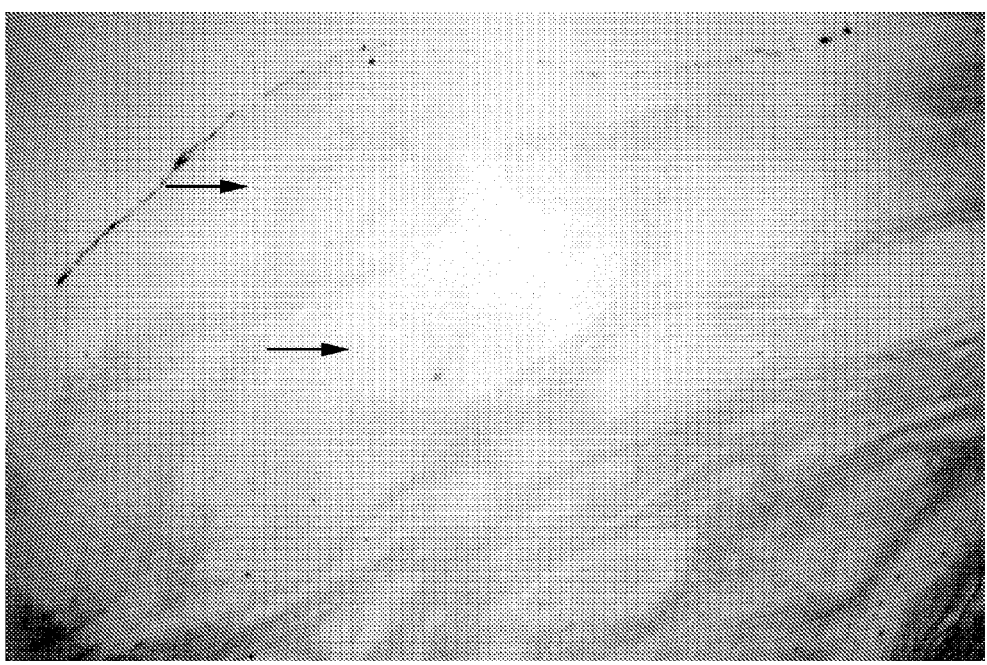

Figure 3. DNA-Histogram of a Condyloma without and with DNAse treatment
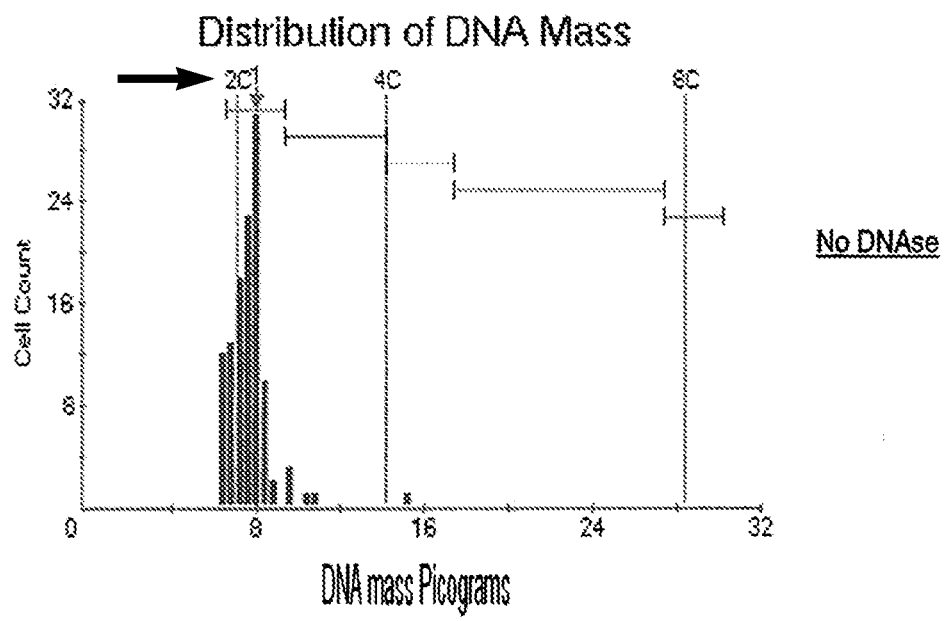
No DNAse
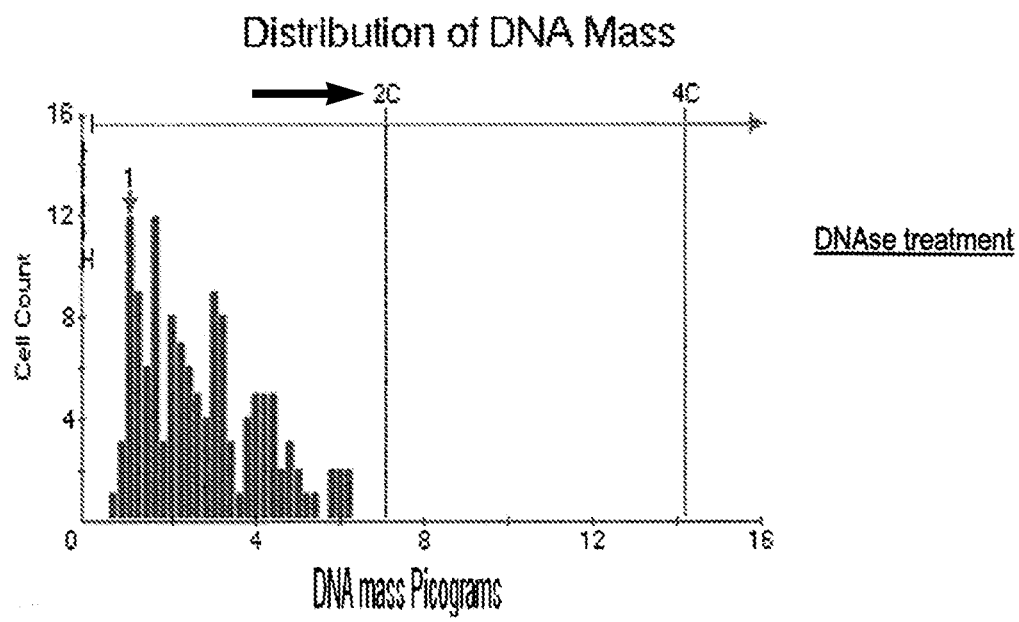
DNAse treatment Figure 4A. In-Situ Hybridization stain Condyloma
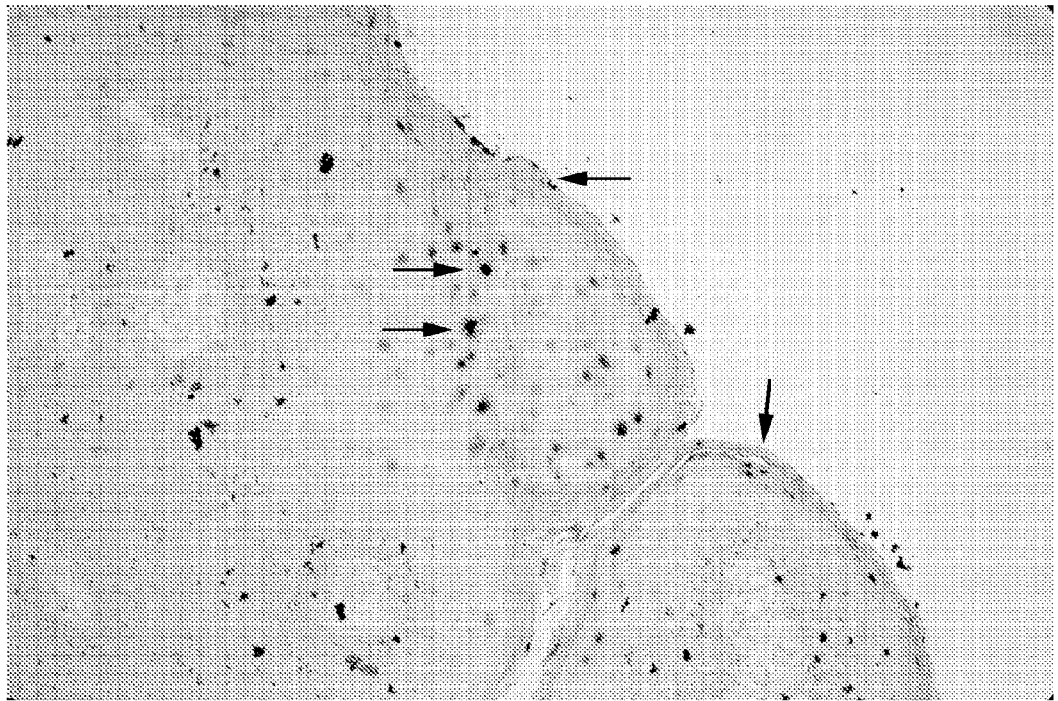
Figure 4B. DNase stain Condyloma
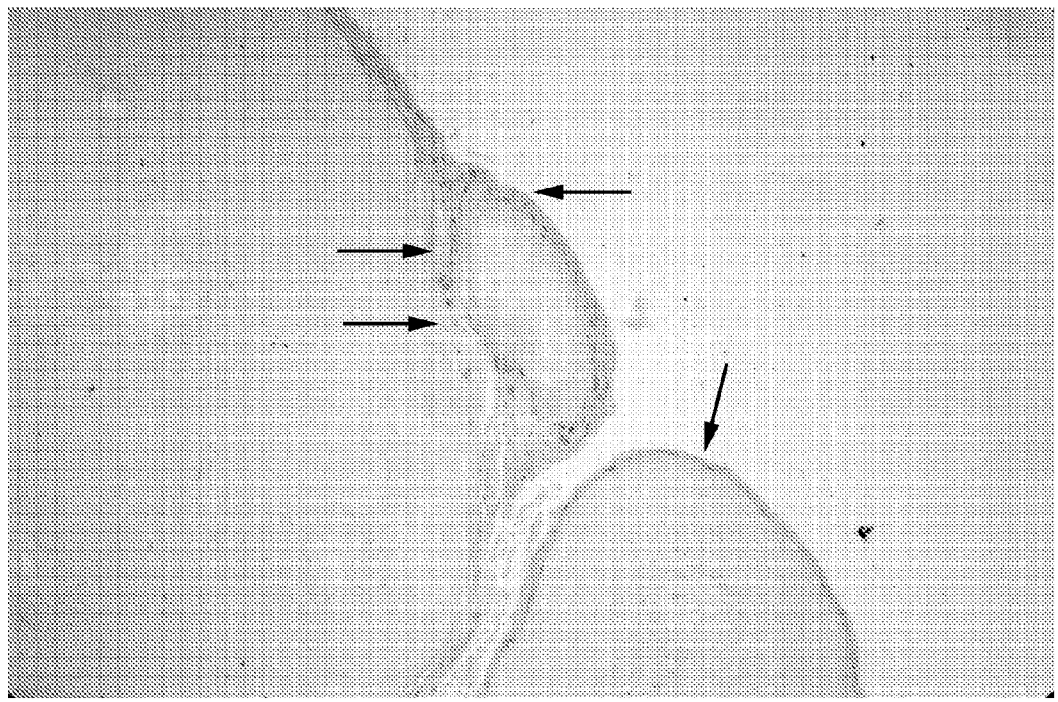

METHOD TO IDENTIFY AND PREDICT DISEASE PROGRESSION OF HUMAN PAPILLOMA VIRUS-INFECTED LESIONS

This application is a continuation-in-part application of International Application No. PCT/US2009/049539, filed Jul. 2, 2009, which claims the benefit of U.S. Ser. No. 61/078,050, filed Jul. 3, 2008. The entire contents and disclosures of the preceding applications are incorporated by reference into this application.

Throughout this application, various references or publications are cited. Disclosures of these references or publications in their entireties are hereby incorporated by reference into this application in order to more fully describe the state of the art to which this invention pertains.

FIELD OF THE INVENTION

This invention relates to methods of identifying and predicting disease progression of human papilloma virus-infected lesions.

BACKGROUND OF THE INVENTION

Cervical cancer screening programs are effective in preventing cancer and reducing mortality (1); however, there are limitations. Cervical cancer and the pre-malignant lesions (cervical intraepithial neoplasia grades I-III, corresponding to mild, moderate and severe dysplasia) are caused by the human papilloma virus (HPV) (2, 3). Most women who acquire HPV develop transient or subclinical infections (4, 5); very few women with HPV infections will progress to cervical intraepithial neoplasia grade II or III (CIN II or III) or cancer (4, 6-7). The major limitations of cervical cancer screening programs arise from the fact that Papanicolaou (Pap) smears and even biopsy can not distinguish benign transient HPV infections from those HPV lesions that will progress (4,7,8). Annually in the United States approximately 50 million women receive Pap smears (9); this results in 3.5 million women requiring follow-up cytology or further colposcopic evaluation for cytologic abnormalities (10). Yet, most of the women diagnosed with minor cytologic abnormalities will have an abnormal pap smear due to a self limiting HPV infection (4, 8). The cost attributed to the follow up of an abnormal Pap smears and the treatment of cervical neoplasia in the United States in 2000 was $2.7 billion (11).

Treatment of cervical neoplasia is costly, since patients referred to colposcopy that are diagnosed with low grade cervical lesions (CIN grade I or HPV infection) continue to be problematic even after biopsy. Again there are no clinically approved methods to distinguish transient HPV infection from HPV lesions that will become precancerous or cancerous (8). Therefore, all women diagnosed with cervical intraepithelial neoplasia grade I or HPV infections after colposcopy and biopsy require follow up. Current management guidelines for the treatment of CIN require that all patients follow one of the recommended protocols (12). These include cytology, colposcopy, and combinations of cytology and colposcopy and HPV DNA typing at various intervals (12, 13). These recommendations are supported by key medical associations including the American College of Obstetrics and Gynecology (12). The diagnosis of CIN grade 1 or HPV infection leads to multiple medical office visits and various repeat tests having to be performed to ensure that patients do not progress to higher grade lesions or cancer. However, it is well known that only 10% of patients with low grade lesions (CIN I or HPV infection) will subsequently develop CIN II, III or cancer in the next 2-years (14). Most patients with low-grade lesions will spontaneously regress (60%) and the remaining will have persistent disease (7, 13). Colposcopy and directed biopsy, which is the standard of care, is not sensitive in predicting disease outcomes in patients with CIN I or HPV infected lesions (15, 16). Furthermore, some clinicians tend to over treat these low grade lesions when they become persistent on repeat colposcopy and biopsy. The concern is that these patients may develop high grade dysplasias and it is difficult to identify these women with available tests. However, current methods used for the treatment of CIN can have clinical consequences especially in young women. Studies show that both ablative and excisional modalities used on the cervix can lead to an increased risk of preterm delivery, low birth weight and premature rupture of membranes (17, 18, 19). In recent years HPV DNA typing for oncogenic strains has been introduced into cervical cancer screening programs. However, up to 85% of patients with low grade cervical lesions will have high-risk HPVs identified making stratification difficult based on type alone (20).

Therefore, to date cervical cancer screening programs suffer from several limitations. Most of these limitations result from the inability of current clinically approved methods to distinguish transient HPV infections from true premalignant cervical lesions. The inability of current laboratory methods to distinguish these two entities affects Pap smear screening. It leads to high number of abnormal cases diagnosed with minor cytologic abnormalities (8). These abnormal pap smears then result in an excessive number of referrals for colposcopy and biopsy (21). Cases that are confirmed on colpscopy to be low grade lesions then require multiple office visits and testing for surveillance (12). Finally, some women with persistent low grade disease tend to be over treated for concerns of progression. The treatment modalities used are now recognized as having potentially serious consequences on future pregnancies, since they can affect normal cervical function (17, 18). Clearly, there is a need to improve current laboratory methods to reduce excessive costs, invasive testing and burden and risks to patients.

SUMMARY OF THE INVENTION

This invention provides a method that can be used to assist cervical cancer screening programs to overcome the disadvantage and limitation of current laboratory methods that fail to distinguish benign HPV infection from HPV related lesions that become precancerous. In one embodiment, the invention is a simple histochemical staining method that can be used to process cervical biopsy specimens to identify lesions that have undergone malignant transformation.

The histochemical staining method relies on the well-known fact that cervical cancers and the premalignant cervical lesions are caused by the human papilloma virus (HPV) (2, 3). In benign lesions, HPV-DNA is extrachromosomal, often packaged into virions (22, 23). However, during malignant transformation HPV DNA becomes chromosomally integrated. This disrupts the life cycle of HPV; as a consequence virion assembly stops (17, 18). The staining method disclosed herein relies on the concept that only benign tissue contains virions with HPV DNA. If this tissue is exposed to enzymatic DNA digestion, cells containing DNA packaged and protected within the protein capsid of the virions will contain undigested DNA (26, 27, 28). In contrast, in HPV-infected lesions that have undergone malignant transformation, no virions are present (22, 29, 30). Therefore, if high grade dysplasias or cervical cancer lesions are exposed to enzymatic DNA digestion, residual DNA will not be present in the cells. The invention is based on identifying extrachromosomal DNA associated with viral particles in benign lesions by a simple histochemical process, not by complex molecular laboratory techniques. Cervical biopsies are processed from routine paraffin-embedded tissue blocks. A slide is cut for staining and then bathed in an endonuclease solution for nuclear DNA digestion. After this treatment any residual DNA can be stained with any convenient DNA-specific reagent in a standard procedure such as the Feulgen process (31). HPV-infected tissue or low grade lesions (cervical intraepithial neoplasia grade I) will demonstrate stained residual DNA, since these lesions contain HPV virions with protected DNA. In high grade dysplasias (CIN grade II or III) or cervical cancer this process will results in no residual stained DNA. The presence or absence of stained residual DNA after process involving DNAse treatment can serve as a marker to identify HPV-transformed cells and aids in the histologic diagnosis of high grade cervical intraepithial neoplasia (CIN II or III) or cancer.

Furthermore, the invention can assist in the management of women that have undergone colposcopy and have a biopsy-confirmed diagnosis of CIN I or HPV infection. Residual DNA positivity or negativity with the present DNAse method can predict disease regression or progression, since HPV DNA changes occur before histologic changes can be seen by light microscopy. Another object of the invention is that it can be used to process other HPV-related tissue specimens (lung, oral, vulvar, penile, anal, etc.) to detect malignant transformation. The invention can also be applied to other clinical samples besides biopsy specimens, particularly pap smears. The method can be used to identify premalignant from malignant cells on cytology. This can assist in triaging which patients with an abnormal pap smear should be referred to colposcopy or followed with repeat cytology. Another object of the invention is that it can be used in conjunction with current FDA-approved HPV typing assays to distinguish benign HPV infections from HPV-infected tissue undergoing malignant transformation. Currently, only the presence or absence of high risk HPV strain can be obtained using these clinical assays. The present invention can further aid these assays by giving insight into the state of HPV DNA present in the cellular sample. The method disclosed herein distinguishes extrachromosomal DNA from integrated HPV DNA (via absence of viral particles), thereby identifying HPV-infected lesions undergoing transformation.

The present invention details a staining process and application for examining HPV infected tissue to determine malignant transformation, by examining susceptibility to enzymatic nuclear digestion. Bovine DNAse I was tested; however, other endonuclease or enzymes with DNase activity may have more specific digestion patterns for high grade CIN. One of ordinary skill in the art would readily select an optimal enzyme for DNA digestion.

Furthermore, the present invention presents a novel concept by which benign HPV infected tissues may be examined for malignant transformation based on the presence or absence of virions. Although a histochemical method for virion identification is described herein, it is feasible to identify HPV virions by combining well known methods routinely used for diagnostic pathology with the present invention. Currently, one of ordinary skill in the art could readily produce antibodies that recognize HPV virions in tissue. These antibodies could be used to develop an immunohistochemistry assay to identify HPV virions in the present invention. Other techniques that identify HPV virions are also feasible and can be used with the method disclosed herein.

BRIEF DESCRIPTION OF THE DRAWINGS

FIG. 1A shows a hematoxylin and eosin (H&E) stained sections from a cervical biopsy specimen demonstrating a condyloma accuminata (non-dysplastic HPV-infected lesion). A parallel section was cut from the paraffin-embedded tissue block. This section was stained as described herein (FIG. 1B). Residual DNA appeared in the cells that have viral particles present, corresponding to the diagnostic region on the H&E slide. Virions interfere with enzymatic DNA digestion; therefore, only in benign HPV-infected cells will residual DNA be stained with the present method. The stained DNA appeared as dark spot within the nucleus (arrows).

FIG. 2A shows an H&E stained section from a cervical biopsy specimen demonstrating a high grade dysplasia case (CIN grade III). The arrow marks the region with epithelial changes characteristic of severe dysplasia. A parallel section was cut from the paraffin tissue block and stained with the DNAse method disclosed herein (FIG. 2B). After DNA digestion, no residual DNA was identified in any regions corresponding to the dysplastic epithelium. HPV lesions that have undergone transformation do not produce complete virions. Therefore, residual DNA is seen not seen after enzymatic DNA digestion in any high grade dysplasia or cervical cancer.

FIG. 3 shows a DNA-histogram of a condyloma case. DNA content was measured using the CAS 200 image analysis system. DNA mass was quantitated by examining a Feulgen-stained slide without DNAse treatment (top panel). Most cells were diploid, 2C or 7.18 pg (black arrows). A few cells in this case were polyploidy (>4C). In contrast, after DNAse treatment and Feulgen staining with the present method, cells that had residual DNA in the condyloma were hypodiploid, <2C (arrow) (bottom panel). Most cells had an average DNA mass of 3.8 pg. The image analysis data confirmed that nuclear staining with the present DNAse method resulted in partially digested DNA within nuclei, confirming the hypothesis that in benign HPV lesions containing virions areas of residual DNA occur after DNAse treatment. In contrast, no measurable DNA content was seen in high grade lesions or cancer by image analysis.

FIG. 4A shows a section from a condyloma accuminata specimen stained with an in-situ hybridization kit using a HPV 16/18 probe. Strong nuclear staining was observed in areas marked by the arrows. A parallel section was cut from the same tissue block and stained with the DNAse method disclosed herein (FIG. 4B). Similar regions were also stained. Corresponding areas identified with the complex in-situ hybridization method can also be seen with the present simple histochemical stain (arrows). The in-situ/DNAse stain comparisons highlight the fact that residual DNA positivity with the method disclosed herein is associated with HPV DNA regions.

DETAILED DESCRIPTION OF THE INVENTION

The present invention relates to the identification of a novel biomarker that can be used to identify low grade cervical lesions from high grade dysplasia and cervical carcinoma lesions. This biomarker called Nuclease Resistant DNA is obtained through a simple histochemical process. The inventor developed this histochemical process based on the well-known fact that essentially all cervical carcinomas and the precursor cervical lesions (cervical intraepithelial neoplasias grades I to III) are associated with the human papilloma virus (2, 3, 5, 8, 22). This simple histochemical process is based on observations and data obtained from sophisticated molecular studies evaluating the physical state of HPV DNA in premalignant and malignant cervical lesions (23,24,25) and from electron microscopy studies examining virion assembly in precancerous and cancerous tissue (22,29,30). In benign lesions, HPV DNA is known to be extrachromosomal, often packaged into virions. However, a key step of malignant transformation is that HPV DNA becomes chromosomally integrated into human DNA (2, 22, 23). This disrupts the natural life cycle of HPV, and as a consequence viral particles are no longer produced. This observation was confirmed by electron microscopy data that show high grade dysplasias or cancers have no viral particles, while adjacent precursor areas with mild dysplasia or just HPV infection contain cells with viral particles (3).

The present invention was conceptualized on the difference between benign HPV lesions from those that have undergone malignant transformation with respect to presence of viral particles in these lesions. It is proposed that if benign HPV-infected tissue was exposed to enzymatic DNA digestion, only cells containing DNA packaged and protected within the protein capsid of virions would contain undigested DNA. In contrast, HPV-infected tissue that had undergone malignant transformation would not contain undigested DNA, since virions are not present. This hypothesis was tested by examining cervical biopsy specimens from paraffin-embedded tissue blocks. Condyloma accuminata (non-dysplastic HPV-infected lesions), CIN grade I to III, and cervical cancer specimens were obtained. After exposure to enzymatic DNA digestion, residual DNA was seen only in low grade specimens. Staining occurred in 81% of condylomas, 80% of CIN I cases and 0% in CIN II and III and 0% of carcinoma lesions (Example 1). This undigested DNA is called "Nuclease Resistant DNA". The present method describes a simple histochemical process that can have laboratory applications to aid in the diagnosis of HPV-transformed tissue specimens, such as severe dyplasia and cervical cancer.

Furthermore, the present invention has clinical applications as well. The method disclosed herein can predict disease progression of low grade cervical lesions (HPV infection and CIN I) to high grade dyplasias, and thereby assist in the management and follow-up of patients with these diagnoses. Currently, there are no clinically approved methods to assist in the management of patients with low grade cervical lesions that can predict disease regression or progression. Therefore, this method can be used to select and identify patients who may need more intensive follow-up, while triaging other patients to less testing and medical office visits. A major advantage of this invention is that it does not rely on molecular or genetic techniques. Rather, it is a simple histochemical method that can be easily adopted by clinical laboratories. Furthermore, by its simple design, it does not use expensive materials or reagents. Therefore, this invention is not only simple to institute but also costs less than most traditional tumor marker assays.

In one embodiment of this invention, Nuclease Resistant DNA can serve as a marker to assist in the diagnosis of cervical intraepithelial neoplasia grade on histology. When CIN grade is diagnosed, the reliability of the diagnosis is problematic, since the histologic diagnosis of CIN relies on subjective interpretation of cellular findings and morphology (32-34). Several studies have shown that even when an expert panel of pathologists reviews CIN cases, agreement is poor and suboptimal (33). Poor diagnostic accuracy and reproducibility can complicate and affect patient care. Incorrect classification of CIN grade on biopsy can lead to inappropriate follow-up or treatment of patients. Clinicians risk over-treating benign lesions or mismanaging precancerous lesions. The present invention provides an adjunct to routine histology, since Nuclease Resistant DNA positivity was found in 0% of high grade dysplasia cases (CIN II-III) and 0% of cancer cases (see Table 1). In contrast low grade cases (CIN I and HPV specimens) Nuclease Resistant DNA positivity was about 80%. A combination of histology and a parallel slide of the same region stained with the DNAse method disclosed herein gives insights into the biological behavior of the lesion. The present invention allows the identification of a novel biomarker to distinguish low grade CIN lesions from high grade CIN lesions and cancer, which can be used during routine processing and examination of cervical biopsy specimens.

In another embodiment, Nuclease Resistant DNA can further serve as a biomarker to assist in the evaluation and diagnosis of cervical cytology specimens. Currently, Papanicolaou (Pap) smears obtained during cervical cancer screening suffer from the same limitations that occur during processing of cervical biopsy on histology. Changes due to transient HPV infections can not be distinguish from precancerous HPV lesions in women that have minor cytologic abnormalities on Pap smear (4, 8). Again, morphology of cervical cells on cytology can not predict biological behavior, therefore, all women diagnosed with low grade squamous intraepithelial lesions (mild dysplasia on cytology) or HPV infection on pap smear get referred to colposcopy and biopsy according to current guidelines (10, 35, 36). However, most women with minor cytologic abnormalities have an abnormal pap smear due to a self limiting HPV infection (4, 8). The present method can be performed on cervical cytology specimens to examine the presence of Nuclease Resistant DNA. Experiments on histology show that high grade lesions and cancer had 0% Nuclease Resistant DNA positivity, while low grade lesions had 80% (demonstrated in Example 1). Therefore, cytology which consists of exfoliated cells from similar regions as examined on biopsy would contain the same Nuclease Resistant DNA staining pattern. Cells from high grade lesions and cancer would not stain while low grade lesion would have a high frequency of Nuclease Resistant DNA positivity. Women with pap smears showing minor cytologic abnormalities can further be evaluated by having a parallel DNAse stained smear obtained. The results of this DNAse smear can assist in triaging patients to either colposcopy versus routine cytology.

An advantage of the method disclosed herein is that it can be readily incorporated into the steps currently used to obtain pap smears in women. The preferred method for obtaining a cervical cytology sample is to use a liquid-based cytology method (35-37). Cells that are scraped from the cervix are place in a small glass vial containing preservative fluid for processing and staining. Two FDA-approved liquid based cytology methods are used, they include THINPREP®, (Cytyc Corp, Marlborough, Mass.) and SUREPATH™, (TriPath Imaging Inc., Burlington, N.C.). Once a routine pap smear is obtained the remaining cells in the container can have an endonuclease enzyme added for nuclear digestion. After an incubation period another smear can be obtained for residual DNA staining. The liquid-based containers are generally kept in clinical laboratories for about a two-week period. If a pap smear is diagnosed with a low grade lesion, rather than sending all of these patients to coloscopy, a DNAse smear can be obtained from the archived cytology sample to assist in the evaluation. To further improve detection of abnormal cells in cytology, one can combine the present DNAse method with a counterstain. Examples of these counterstains would include, but are not limited to, antibodies, DNA or RNA probes. These counterstains would highlight HPV-infected cells on cytology and the DNAse method disclosed herein would then mark malignant transformed cells.

In another embodiment, Nuclease Resistant DNA positivity or negativity can be used to distinguish benign HPV infection from truly premalignant cervical lesions in women evaluated by colposcopy and biopsy that are diagnosed with CIN I or HPV infection. Predicting which women with low grade lesions will progress is not currently possible, even with colposcopy and biopsy (8,12). The inability to predict which women will progress to higher grade lesions from those women that will have regression results in all women having to have extensive follow up and testing (13). The limitations of current methods are that transient HPV infection appears histologically similar to HPV lesions that will progress to high grade dysplasia or cancer if left untreated. Data from the experiments show that in all advanced lesions (CIN II to cancer lesions) residual DNA negativity was associated with 100% of these cases, while low grade cases (CIN I and condyloma) had 80% residual DNA staining. Furthermore, cervical cancer and high grade dysplasia often have precursor lesions (HPV and CIN I component) adjacent to the diagnostic area. In the present experiments, the frequency of residual DNA positivity in these low grade regions decreased from 81% in true condyloma and CIN I specimens to 25% in the adjacent areas of cancer cases. These observations suggest that low grade lesions adjacent to high grade dysplasia or cancer cases may look histologically identical to true condyloma and CIN I cases, however, biologically they are distinct and can be distinguished with the DNAse staining method disclosed herein. In addition, there are data showing the present DNAse method can predict colposcopic and pathologic regression/progression of HPV lesions, over a follow-up period of 12 to 24 months (Example 3). Among HPV (+) patients that develop complete regression of their lesion, 80% of the initial biopsies stained positive with the present DNAse method. In contrast, among HPV (+) positive patients that progressed to CIN grade II or higher, 75% of the initial HPV biopsies stained negative for residual DNA with the present method. Therefore, an embodiment of the present invention is to use residual DNA negativity or positivity to predict disease progression of HPV or CIN I lesions after colposcopy and biopsy. The present invention will allow one to triage patients more specifically based on risk of disease progression, rather than follow all patients with multiple office visits and repeat cytology, HPV typing and colposcopy.

In yet another embodiment, the present invention can be used to process other HPV-related tissue specimens such as lung, oral, vulvar, penile, anal, skin, etc., to detect malignant transformation. Investigators have reviewed the topic of HPV in human cancer (38, 39, 40), and they reported that viral oncogene expression (E6 and E7) can transform a variety of tissues. In addition to cancer of the cervix, a major proportion of anal, perianal, vulvar, and penile cancers appear to be linked to HPV infections. In addition, around 20% of oropharyngeal cancers contain DNA from the same oncogenic HPV types as in anogenital disease (39). Recent evidence even suggests a possible role of HPV infection in squamous cell carcinomas of the skin (40). Therefore, the present invention has application with these tissue specimens as well. The mechanism for tumorgenesis is not specific to the tissue, but rather to viral oncogene over-expression. Therefore, when transformation occurs, the natural life cycle of HPV is disrupted and susceptibility to endonuclease digestion can be identified with the DNAse stain disclosed herein. The present invention provided a biologic marker for a variety of tissue specimens and a range of tissue samples, such as biopsy, cytology etc.

In another embodiment, the present invention can be used in conjunction with current FDA-approved HPV typing assay kits to distinguish benign HPV infections from HPV-infected tissue undergoing malignant transformation. These commercial kits are only able to confirm the presence or absence HPV DNA and provide typing information regarding which strains may be present. They fail to provide data as to whether HPV has transformed the cellular sample. The present invention can further aid these assays by giving insight into whether extrachromosomal HPV DNA is present versus integrated HPV DNA (via absence of viral particles). A tissue specimen can be tested with these current HPV typing assays in routine fashion, and the presence or absence of HPV DNA can be confirmed. In positive cases a repeat assay can be performed after DNAse treatment. This should digest all nuclear DNA, except DNA associated with viral particles in benign HPV-infected tissue. Therefore, if the sample has HPV DNA after DNAse treatment then the sample contains viral particles and benign infection is present. Alternatively, a positive initial HPV typing assay but negative repeat test after DNAse treatment would imply malignant transformation. Complete nuclear digestion occurs in tissue that is transformed, as seen in experiments measuring residual DNA mass in high grade lesions and cancer by image analysis (Example 1). Therefore, DNAse treatment is expected to digest all nuclear material in transformed tissue. Commercially available HPV typing kits include, HYBRID CAPTURE II (Digene, Gaithersburg, Md.), PATHOGENE®, BIOPAP® (Enzo Diagnostics, Farmingdale, N.Y.), etc.

In another embodiment of the present invention, there is provided a staining process and an application for examining HPV-infected tissue, to determine malignant transformation by examining susceptibility to enzymatic nuclear DNA digestion. In the present experiments, susceptibility to bovine endonuclease DNAse I was tested, however, there are other enzymes that are well suited to be used in the method disclosed herein (41, 42, 43). These endonucleases have different DNA recognition sites, thereby digesting cellular DNA differently. It is conceivable that other endonucleases, either alone or in combination, can digest HPV infected lesions more specifically than DNAse I to predict HPV progression. In the present study low grade cases (HPV or CIN I) had 80% residual DNA positivity, and thus 20% residual DNA negativity. From the natural history of HPV infection, most low grade lesions represent a transient HPV infection, since only 10% of these cases are known to progress (2, 3). Therefore, what is desirable is that the frequency of residual DNA negativity correlates closely with progression rates of low grade lesions. In one embodiment of the present invention, susceptibility to endonucleases DNA digestion can be evaluated for the different enzymes available, and results can be compared. Conceivably other endonucleases may have a different frequency of residual DNA positivity/negativity distinct from DNAse I. Patients that are known to have CIN I or HPV infection can be followed over a period of time to obtain regression and progression data. Staining experiments involving pre-treatment with various endonucleases can be performed on samples from these patients to determine optimal endonuclease(s) that can be used to predict disease progression. The present invention describes a novel method to examine the spectrum of disease caused by HPV to identify transformation based on susceptibility to endonuclease digestion. One of ordinary skill in the art would readily select an optimal enzyme for DNA digestion.

In summary, the present invention provides a method of predicting the progression or regression of a disease caused by human papilloma virus (HPV) infection in a subject, comprising the steps of: obtaining at least one tissue sample from the subject; digesting the sample with endonuclease; and staining the sample for the presence of DNA, wherein the presence of DNA indicates the disease would regress, and wherein the absence of DNA indicates the disease would progress. In one embodiment, diseases caused by HPV infection include benign HPV infection or cervical intraepithelial neoplasia grades I to III. In general, endonucleases applicable in the present invention include, but are not limited to, DNAse I, DNAse II alpha, DNAse II beta, endodeoxyribonuclease, genetically engineered endonucleases, and DNAase such as Benzonase® (Merck Chemicals Ltd, Nottingham, UK). In one embodiment, the tissue samples can be lung tissue samples, oral tissue samples, vulvar tissue samples, penile tissue samples, anal tissue samples, skin samples, cervical biopsy specimens or Pap smears. DNA staining can be performed according to standard procedures such as Feulgen process or any other DNA staining that may enhance identification of DNA. Examples of DNA staining include, but are not limited to, thionin staining, gallocyanin chromalum nuclear staining, Cuprolinic Blue staining, fluorescence DNA staining, hematoxylin staining, antibody DNA staining or DNA staining using a molecular probe, or any variant or combination of the above described DNA staining methods. In addition, it may be possible to biochemically alter the main staining reagent in the standard Feulgen process, the schiffs reagent (also known as pararosaniline, rosaniline, magenta, or basic fuchsin). Altering the ring structures of the schiffs reagent via organic synthesis may enhance the color of DNA staining. In another embodiment, counterstaining is performed on the samples to improve detection of abnormal cells. Counterstaining can be performed using protocols and agents well-known in the art. For example, counterstaining can be performed using antibodies, DNA or RNA probes that bind to HPV components or tumor antigens or antigens of dedifferentiation.

The present invention also provides a method of distinguishing benign human papilloma virus (HPV) infection from at least one malignant lesion in HPV-infected tissue in a subject, comprising the steps of: obtaining at least one tissue sample from a subject; digesting the sample with endonuclease; and staining the sample for the presence of DNA, wherein the presence of DNA indicates benign HPV infection in the samples. Endonucleases applicable in the present invention have been described above. In one embodiment, the tissue samples can be lung tissue samples, oral tissue samples, vulvar tissue samples, penile tissue samples, anal tissue samples, skin samples, cervical biopsy specimens or Pap smears. In another embodiment, the tissue samples have been or are further examined in HPV typing assays. In the cases where the tissue samples are cervical biopsy specimens or Pap smears, the detection of DNA indicates there is benign HPV infection or cervical intraepithelial neoplasia grade I in the samples, whereas absence of DNA indicates cervical intraepithelial neoplasia grade II or grade III, or cervical cancer in the samples.

The present invention also provides a method of detecting malignant transformation in tissue samples from a subject with human papilloma virus (HPV) infection, comprising the steps of: obtaining at least one tissue sample from a subject; digesting the sample with endonuclease; and staining the sample for the presence of DNA, wherein the absence of DNA indicates there is malignant transformation in the tissue samples. Endonucleases, as well as tissue samples and DNA staining, applicable in the present invention have been discussed above.

The present invention also provides a method of identifying an endonuclease suitable for use in any of the methods described above, comprising the steps of: obtaining a first tissue sample comprising benign HPV infection; obtaining a second tissue sample comprising malignant HPV infection; digesting the first and second tissue samples with an endonuclease; and staining the tissue samples for the presence of DNA, wherein a higher level of DNA staining in the first tissue sample as compared to the second tissue sample indicates that the endonuclease is suitable for use in any of the methods described above. In general, the DNA staining methods and tissue samples described above can be used in this method. In one embodiment, the tissue samples are cervical biopsy specimens or Pap smears. In another embodiment, the benign HPV infection in the first tissue sample can be cervical intraepithelial neoplasia grade I, whereas the malignant HPV infection in the second tissue sample can be cervical intraepithelial neoplasia grade II or III.

In one embodiment, the present invention presents a novel concept by which benign HPV infected tissues may be identified when undergoing malignant transformation, based on the presence or absence of virions. Though a histochemical method is presented to identify virions, based on the susceptibility to endonuclease digestion, it is feasible to identify HPV virions by combining well known methods routinely used for diagnostic pathology with current HPV technology. It is now feasible to produce antibodies that recognize HPV virions in tissue for use in cytology or for paraffin embedded tissue biopsies. These antibodies could be used in an immunohistochemistry assay. Commercially available laboratories exist that can produce antibodies for staining, if an appropriate antigen is proved. It is possible to develop an antibody to the HPV virions by producing HPV L1 viral like particles (VLP). This technology is well established and has led to the development of two FDA-approved HPV vaccines, Gardasil® by Merck Pharmaceuticals and Cervarix® by Glaxosmithkline. A recent review on this topic has been published (Garland S M, et al. Human papillomavirus vaccines: current status and future prospects. Drugs 2010 Jun. 18; 70(9):1079-98). Briefly, the HPV capsid is composed mostly of the L1 protein and very small amounts of the L2 protein (2). When the L1 gene is transfected into a cell culture system it forms monomers that spontaneously form capsomers or a virus like particle (VLP). These VLPs resemble native HPV virions when examined by electron microscopy. Methods for the preparation of VLPs are well known in the art, and include VLP disassembly-reassembly approaches that are described in WO09913056 and U.S. Pat. No. 6,245,568. VLPs induce antibodies in humans and animals. The antibodies produced recognize the conformational epitopes of L1 and these antibodies cross react with the naturally occurring HPV capsid antigen in the assembled virion. These antibodies are very specific such that it produces immunity and prevents HPV infection (Rose R C, et al. Serological differentiation of human papillomavirus types 11, 16 and 18 using recombinant virus-like particles J Gen Virol 1994 September; 75 (Pt 9):2445-9).

Therefore, VLPs can be used to produce anti-HPV virions antibodies to be used in an immunohistochemistry assay. VLPs can contain functional or truncated or derivative forms of L1 protein from high risk HPV types, such as HPV 16, HPV 18, HPV 31 and HPV 45, etc. These VLPs can be of single HPV type or a mixture of VLPs from different HPVs. The L1 protein or derivative may also be a fusion protein, such as the fusion of the L1 protein with the HPV L2 protein. VLP formation can be assessed by standard techniques such as, for example, electron microscopy. One skilled in this art could produce optimal VLPs to be developed for an immunohistochemistry assay. Either monoclonal or polyclonal antibodies could be synthesized for use.

Although the L1 protein or its derivatives have been used to form VLPs for the purpose of vaccine development, to date, VLPs have not been used to create an immunohistochemistry assay to identify HPV virions in tissue specimens. Anti-HPV L1 antibodies have been synthesized and are commercially available for use in immunohistochemistry. These antibodies have not been tested to determine whether they recognize the conformational three dimensional HPV L1 epitope or the linear L1 epitope or both. It is proposed that by combining current technology with the present invention it is feasible to produce antibodies to native HPV capsid proteins to identify virions in tissue.

In one embodiment, the present invention provides a method of distinguishing benign human papilloma virus (HPV) infection from the presence of at least one malignant lesion in HPV-infected tissue in a subject, comprising the steps of: obtaining at least one tissue sample from the subject; and utilizing anti-HPV antibodies to identify in the sample the presence of HPV virions, wherein presence of virions indicates benign HPV infection, and wherein absence of virions indicates the presence of at least one malignant lesion in the tissue of the subject. In another embodiment, presence of virions indicates a disease caused by HPV would regress, and wherein absence of virions indicates the disease would progress.

In general, the anti-HPV antibodies used in the above method can be antibodies that recognize HPV L1 protein, antibodies that recognize HPV L2 protein, or antibodies that recognize HPV capsid antigen. The anti-HPV antibodies may recognize truncated or derivative forms of HPV L1 protein, wherein the HPV L1 protein is derived from HPV types HPV 16, HPV 18, HPV 31, or HPV 45. Alternatively, the anti-HPV antibodies can recognize HPV L1 protein or HPV L1 fusion protein. Various tissue samples such as lung tissue samples, oral tissue samples, vulvar tissue samples, penile tissue samples, anal tissue samples, cervical tissue samples, and skin samples can be used in the method described above.

In another embodiment, the present invention also provides a kit comprising reagents and instructions for practicing the methods described herein.

In summary, the present invention provides a novel approach to identify HPV associated lesions that are undergoing transformation bases on the absence or presence of HPV virions. A method to identify HPV virions is disclosed herein; however, other techniques that identify HPV virions are feasible and can be used with the present invention.

The invention will be better understood by reference to the Experimental Details which follow, but those skilled in the art will readily appreciate that the specific experiments detailed are only illustrative, and are not meant to limit the invention as described herein, which is defined by the claims which follow thereafter.

Throughout this application, various references or publications are cited. Disclosures of these references or publications in their entireties are hereby incorporated by reference into this application in order to more fully describe the state of the art to which this invention pertains. It is to be noted that the transitional term "comprising", which is synonymous with "including", "containing" or "characterized by", is inclusive or open-ended and does not exclude additional, un-recited elements or method steps.

EXAMPLE 1

Protocol for the DNAse Staining Method

From paraffin-embedded tissue blocks, two 4 micron sequential sections were cut on a standard rotary microtome, and placed on positively charged slides (Surgipath-Snow coat X-TRA, Richmond, Ill.). The sections were dried for twelve hours in a 56 degree Celsius oven, then deparaffinized. One of the sections was placed in a bath containing the bovine pancreatic endonuclease DNAse I for DNA digestion. This process has been previously described and used by investigators to identify intranuclear DNA inclusion bodies associated with viral particles (26-28, 44). This protocol was modified and include steps to enhance residual HPV DNA staining as follows:

Day 1
Slides kept overnight in 37° C. incubator to deparaffinize the sections.
Day 2
Dip in Xylene: 5 mins×2
Bring out through gradient of ethanol solutions
Dip in water thoroughly
DNAse digestion step: 0.02% DNAse solution+buffer sol. overnight.
Day 3
Wash in water thoroughly: 5 mins
Dip slides in 1 N HCl×10
Place sections in 5 N HCl for 1 hour
Re-dip slides in 1 N HCl×10
Basic Fuchsin stain: 2 Hrs
Sulfurous wash: 5 mins×2 times (in 2 different baths)
Place slide in 96% ethanol: 5 mins
Place slide in Orange G sol. (0.025 g): 15 secs
Put the slides in 96% ethanol: 5 mins×2 times
Put slides in 100% ethanol: 5 mins×2 times
Place slides in Xyelene: 5 mins×2 times
Mount the slides
Leave slides to dry at room temp overnight.
Reagent Preparation
DNAse Reconstitute Buffer
50% glycerol
10 mM tris HCl pH 7.5
10 mM CaCl2
10 mM MgCl2
DNAse I solution: DNAse (powdered form, Sigma Aldrich Chemicals, USA)+Reconstituted DNAse buffer
Sulforous Wash
Distilled water: 300 ml
1 N HCl: 15 ml
10% Na metabisulfite: 18 ml
Orange G
0.025 g Orange G
99 ml 96% ethanol
1 ml glacial acetic acid For parallel comparison the other section was processed in bath without DNAse. Although the present example uses DNAse I to validate the hypothesis, the present invention can use other endonucleases. Other enzymes could have a more specific association in predicting grade and progression of CIN lesions. The present invention embodies a novel concept in which HPV-infected tissue can be separated into those lesions that contain a benign HPV infection from those lesions that have been transformed by subjecting the tissue to nuclear digestion and examining residual DNA content. Representative examples of endonucleases applicable in the present invention include, but are not limited to, a well known group such as DNAse I, DNAse II, EcoRI, Hind II, Hind III, exonuclease III, XhoI, etc., as well as novel genetically engineered endonucleases offering both DNAse and RNAse activity such as Benzonase® (Merck Chemicals Ltd, Nottingham, UK).

In the present experiments, any residual DNA was selectively stained after nuclear digestion. All tissue slides were exposed to a Feulgen stain using the CAS (Cell Analysis Systems, Elmhurst, Ill.) DNA staining kit. This is a commercially available stain and reagent system (31). The Feulgen stain specifically stains DNA blue and enables quantitative measurements of DNA to be obtained (45). Cytoplasmic counterstaining with orange-G was performed to facilitate identification of the nuclei. One of ordinary skills in the art would readily employ other staining methods specific for DNA, such as thionin staining, gallocyanin chromalum nuclear staining, Cuprolinic Blue stains, fluorescence DNA staining methods such as acrindine orange, or even routine hematoxylin staining.

EXAMPLE 2

DNAse Staining with Cervical Biopsy Tissue

The following experiments consisted of examining cervical biopsy specimens. Hematoxylin and eosin (H&E) stained sections were examined from seventy-eight cases containing the following histology diagnoses: 17 invasive cervical carcinomas, 15 CIN grade III cases, 15 CIN II, 15 CIN I, and 16 condyloma accuminata (non-dysplastic lesions with characteristic changes of HPV infection). Each case was reviewed by at least two independent pathologists to confirm the diagnosis. Controversial cases were re-examined by the most senior pathologists for a final diagnosis. For each case, the area of interest was identified by reviewing the H&E slides. The main area containing the diagnostic regions on the slide were marked with ink to easily compare with DNAse-treated slides. In addition, in high grade dysplasia (CIN II and III) and cancer cases the adjacent regions to the diagnostic areas were also examined.

High grade dysplasia and cervical cancer develop from well-defined precursor lesions (2,3). As a result, the adjacent regions often contain low grade components (CIN I and HPV areas). Therefore, these precursor lesions were also examined. These coexisting adjacent regions were also examined for residual DNA positivity. This was done because the low grade component of severe dysplasia and cancer cases may histologically look like CIN I and HPV lesions in patients that have a transient benign infection; however, it is expected that residual DNA staining in these two cases would be different since the present method is identifying a biological difference. Finally, histologically normal skin and verruca vulgaris specimens were used as positive and negative controls during each staining experiment.

Residual DNA Measurements: Digital Image Analysis

In addition to examining nuclease resistant DNA positivity, quantitation of residual DNA was done for each cases, using the CAS 200 IMAGE ANALYSIS SYSTEM (Becton-Dickinson, Inc, Elmhurst, Ill.). This was done to confirm that nuclei observed to have DNA staining after DNAse treatment were actually partially digested nuclei. In addition, DNA mass of positive cases was examined. This was done to see if residual DNA mass correlated with cervical lesion grade. DNA content of the selected areas was measured via a cytophotometric process based on the amount of light-absorbent Feulgen stain present (45). In order to measure the DNAse-treated sections, the manufacturer's screening criteria (filter), for selecting and categorizing cells, was modified. The new filter was adjusted for the possibility that DNAse treated nuclei might contain a fraction of the DNA found in whole cells. The filters were adjusted to the most sensitive parameters. The DNA mass of a cell was expressed in picograms (pg) and a DNA histogram was generated for each case. The manufactures diploid internal control is 7.18 pg. This is seen as the 2C area in the generated histograms (depicted in FIG. 3).

Again the areas measured were selected by reviewing the H&E slides. The primary lesion was marked with ink and the corresponding area in the DNAse treated section examined for the presence or absence of residual DNA. All efforts were made to assure that comparable fields were measured.

In-Situ Hybridization

From each diagnosis 2 cases were selected to have in-situ hybridization performed on the tissue slides. These ten cases were selected to confirm that the nuclease-resistant DNA corresponds to HPV-DNA. In addition, an attempt was made to determine whether residual DNA positivity correlated with HPV type (high risk oncogenic versus low risk non-oncogenic HPV's). An in situ hybridization detection kit using digoxigenin-labeled probes was obtained from Signet Laboratories (Dedham, Mass.) The kit consists of a pan-screen probe to DNA common to the HPV genus and specific DNA probes to identify types 6/11 (low risk HPV's) and 16/18, 31/31 (high risk HPV's). For comparison, parallel sections was cut for each of the ten cases and stained by DNAse-Feulgen process.

Results

After nuclear digestion with DNAse, residual DNA was observed in 0% of the CIN II, CIN III and cancer cases (Table 1). In contrast, the low grade cases (CIN I and condyloma) had residual DNA identified in most lesions. In condylomas (HPV infection with no dysplasia) the frequency of residual DNA was 81%. In the CIN I specimens, residual DNA was seen in either the CIN I or HPV region in 80% of the cases. In the CIN I cases, both regions (CIN I and HPV areas) were considered together rather than distinctly. Clinically and histopathologically CIN I and condyloma are classified simply as low grade lesions, since the natural history and management are similar. This is in contrast to high grade cases (CIN II to cancer) in which the low grade component is distinguished from the main area, since prognosis and treatment is based on the diagnosis of the predominant area.

The data is summarized and presented in Table 1. The cases that were positive contained clusters of blue fragmented nuclei in the superficial epithelial layers surrounded by an orange cytoplasmic background (FIG. 1B). The sub-epithelial region served as the internal negative control, these cells had pale nuclear regions devoid of any Feulgen blue DNA staining. None of the high grade lesions (CIN II/CIN III) and carcinoma cases had any residual DNA in the primary areas where the dysplastic epithelial cells where located (FIG. 2B). Occasionally, however, the adjacent areas in some of these high grade cases had residual DNA in the low grade component. However, in these adjacent areas only a few cells had residual DNA. In contrast, in the true condlyoma and CIN I cases the slides contained large clusters of positive nuclei. Furthermore, the frequency of residual DNA positivity in these low grade regions (CIN I and HPV) decreased from 81% in true condyloma and CIN I specimens to 25% in the adjacent areas cases. Similarly, residual DNA positivity in the low grade component of the CIN II cases and CIN III cases, were different than the actual low grade specimens, 80% versus 33%, and 80% versus 57%. These observations suggest that low grade lesions adjacent to high grade dysplasia or cancer cases may look histologically identical to true condyloma and CIN I cases; however, biologically they are distinct. Residual DNA positivity is based on virion presence in the cells. Complete viral particle formation only occurs in benign HPV-infected lesions, while the natural life cycle of HPV is disrupted in transformed lesions. Therefore, this nuclease-resistant DNA is a biomarker that distinguishes low grade lesions from high grade dysplasias and cervical cancer.

Finally, in these experiments the positive control had strong positive nuclear staining. The negative control had no residual DNA. Chi square analysis among groups by diagnosis of the main lesion demonstrated statistically significant differences with respect to residual DNA positivity. Low grade lesions (80%) versus high grade dysplasias (0%) ($P<0.00$), and low grades (80%) vs. CA (0%) ($P<0.000$).

DNA Quantitation Experiments

In order to establish that cells seen on histology had digested nuclear DNA material, DNA quantification was performed by image analysis. Each case was examined, and a DNA-histogram was generated representing the DNA content of the positive nuclei. Subsequently, an average DNA mass was calculated for all positive case in each category (FIG. 4). Graphs were obtained for the 25 low grade specimens that stained and for the low grade regions of the 8 CIN II and III cases and the one cancer case. All specimens that had residual DNA positivity had a hypodiploid DNA content (<2C). The mean DNA mass for low grade cases was 3 pg (range 1-5.7 pg). The mean DNA mass of the adjacent areas that stained in the high grade dysplasias and one cancer case was 4.5 pg (range 0.8-5.7 pg), not significantly different. Among lesions that were positive, quantitation of residual DNA did not show any particular DNA mass specific to any cervical biopsy diagnosis. However, the nuclear DNA content in these low grade cells were all less than the normal diploid content (7.18 pg), indicating that nuclei seen on histology contain partially digested nuclear material. These data support the hypothesis that viral particles interfere with DNAse susceptibility. None of the diagnostic areas in the high grade dysplasias or cervical cancers had any measurable residual DNA content by image analysis, confirming the microscopy observations that these cases had 0% staining with the present method.

In-Situ Hybridization Results

Ten cases were used to verify that nuclease-resistant DNA corresponds to HPV-DNA. Serial sections were stained by in-situ hybridization for the presence of HPV-DNA and corresponding regions were stained by the DNAse-Feulgen method disclosed herein (Table 2). The in situ probes stained 3/10 specimens and the DNAse-Feulgen stain stained 3/10 specimens. Though the in situ method produced a more intense nuclear stain, completely identical areas were found in two of the cases (FIG. 4). In the third case that stained with each method, the areas were different. The in situ hybridization stain is a sophisticated, time-consuming method that uses an HPV-specific DNA probe, therefore, it was expected that more cases would be stained with this method, compared to histochemical process. However, performance appeared comparable at least with these few cases. Furthermore, staining with both methods occurred only in low grade specimens. In the high grade dysplasia and cancer cases the in situ stain did not detect HPV DNA, probably due to the very low amounts of HPV DNA present in these specimens. In the two cases that stained identically, the residual DNA positive areas were stained by the HPV types 6/11 and 16/18 probes in one case. In the other case, the residual DNA areas were stained by a HPV 31/33 probe. Residual DNA positivity occurs with both high and low risk HPV's; the DNAse stain did not appear to be HPV type specific.

Discussion

This is the first discovery of endonuclease resistant DNA as a novel biomarker for CIN and cervical carcinoma. Previously, investigators have used endonuclease treatment to process tissue specimens to identify intranuclear DNA inclusion bodies associated with viral particles (26-28, 44). The present invention modified this method and applied it to the spectrum of disease that leads to cervical cancer. It is tested that the present staining method could discriminate between benign HPV-infected tissue from precancerous and cancerous lesion of the cervix. Though, it is well known that HPV is associated with cervical cancer and the precursor cervical lesions, the virus exists in different states in these lesions. The method disclosed herein distinguishes HPV lesions that have undergone transformation from those lesions in which HPV is associated with a benign infection. Virions contain extrachromosomal HPV DNA and assembled viral particles only occur in benign tissue. Experiments confirm the hypothesis that viral particles alter resistance to endonuclease digestion and this can be used to distinguish low grade cervical lesions from high grade and cancer cases. In the present experiments residual DNA was not seen in any of the high grade dysplasia (CIN II/III) or carcinoma cases. This was confirmed by image analysis in which no measurable DNA mass was identified cytophotometrically. In contrast, the low grade cases (condyloma and CIN I) had about 80% residual DNA positivity. The histochemical process disclosed herein was able to identify 100% of the high grade lesions and cancer cases. In the low grade specimens there were mixed results, since 20% did not stain. It is known that most of the low grade cases represent a transient HPV infection (2,3). Only in about 10% of these cases will women develop progressive disease in the next 2 years (8,14). Therefore, low grade cases really represent a mixture of two disease entities. One is a transient HPV infection and other a true premalignant state. By far, most of the low grade cases are known to be transient HPV infections. Similarly, in the present study most cases had residual DNA positivity probably reflecting the benign nature of these lesions, at least at the time the biopsy was taken. However, it is expected that not all these low grade cases examined would be benign HPV infections, though histologically they appear similar. Therefore, the frequency of residual DNA negativity (20%) among these low grade cases in the present study is within the expected range of true premalignant lesions based on epidemiologic data. Therefore, negative residual DNA staining may be associated with future CIN I or HPV progression. This conclusion is based on the fact that none of the high grade dysplasia or cancers cases had staining in the diagnostic areas and the adjacent precursor regions in these cases had a significant decrease in residual DNA positivity was well.

Furthermore, the hypothesis that HPV viral particles can alter the susceptibility to endonuclease digestion was validated. The mass of residual DNA was examined by image analysis to confirm that positive nuclei with the present stain did indeed contain undigested DNA fragments. In addition, in situ hybridization was performed to show that these undigested nuclear regions were associated with HPV DNA. The data from the quantitative DNA analysis, with and without DNAse treatment, shows that the quantity of nuclease resistant DNA is hypodipliod. The mean DNA content for the low grade cases that stained were 3.0 pg (range 1.0-5.7 pg). The mean DNA mass of the areas that stained in the high grade dysplasia and cancer cases was 4.5 pg (range 0.8-5.7 pg). This DNA content consisted of about 40%-60% of the normal DNA mass of nuclei in tissue slides not treated with DNAse. Possibly this DNA quantity is not solely viral; rather, it is a mixture of both viral and partially digested human DNA. Regardless, the DNA content analysis confirms that viral particles can alter susceptibility to nuclear digestion. Furthermore, in high grade dysplasias and cancers, which are expected not to contain virions, had no measured residual DNA. Finally, the in situ hybridization data confirmed that residual DNA was associated with HPV DNA. In the two cases that stained homologous regions stained with both the DNAse stain and the in situ hybridization method (FIG. 4). Though, only low grade cases stained with both methods, they appeared to perform equally in identifying HPV in paraffin-embedded tissue. The DNAse stain may be a quick screen for examining location of HPV on histology specimens, instead of doing complex time consuming molecular imaging. Finally, the DNAse stain did not appear to be HPV type-specific.

EXAMPLE 3

The Relationship of Residual DNA Status and Clinical Outcome of HPV Infection

A pilot study was done to examine women that were seen in a Colposcopy Center to determine if the DNAse method disclosed herein could predicte disease outcomes of women found to be HPV (+) over a 12-24 months follow-up period. Patient records were searched to identify women initially diagnosed with HPV infection by colposcopy and biopsy, and confirmed by HPV DNA testing for high risk types (oncogenic types). Medical records were reviewed for women that either had complete regression of HPV by colposcopy, biopsy, cytology and HPV testing, or progressed to CIN grade II or higher. Records were evaluated until 10 HPV (+) patients were found that had complete regression of their infection and 8 HPV (+) patients found to have progressed to a high grade CIN. The original diagnostic HPV tissue block was obtained and a parallel section cut and stained with the endonuclease-DNA method as described in Example 1. The data are summarized in Tables 3 and 4. Patients in the clinic with HPV infection received standardized surveillance. This included repeat colposocopy every 12 months and a pap smear at each colposcopy and also every 6 months. This surveillence protocol was done until patients regressed or progressed to then require further treatment. Of the 10 patients that regressed completely, all were (+) HPV DNA for high risk types and all received a 1-year colposcopy (Table 3). After the 1-year exam, 4 (40%) remained (+) HPV to require another 24 month colposcopy and a third biopsy. Eighty percent of these patients had (+) residual DNA staining of the initial biopsy specimen at the time HPV was diagnosed. In contrast, of the eight HPV (+) patients that progressed to high grade dysplasias most were residual DNA negative (Table 4). Seventy-five percent of these HPV (+) patients that progressed were had no DNA staining with the method disclosed herein at the time HPV was identified. Furthermore, all high grade lesions from these patients were also stained for residual DNA and were all found to be negative, as expected. Currently no clinical test can predict progression or regression outcomes of HPV infected women. Neither colposcopy, biopsy, cytology or HPV testing identified which patients would progress or regress on initial presentation. All patients required a significant amount of resources to be used during the follow-up period. Of the women that regressed all had at least a second 12 month colposcopy for surveillance and 40% of these remained HPV (+) to then have a third colposcopy to finally be found to have complete resolution of HPV. Furthermore, multiple pap smears were needed, obtained at each colposcopy and 6 month intervals. Epidemiologic observations demonstrate that only 10% of HPV positive patients will progress to CIN II or above within 2 years (7,13). Most lesions regress spontaneously and the remainder become persistent infections. Excessive amount of resources are spent monitoring all HPV (+) patients to find the 10% that will advance. Clearly, improvements need to be made to improve costs, reduce resource utilization and avoid unnecessary invasive procedures done to patients. This data confirms that the staining method of the initial HPV biopsy correlates with progression/regression outcomes over a 12-24 month follow-up period.

TABLE 1

DNAse Staining With Cervical Biopsy Specimen

| Histology Cases (Number) | Residual DNA Positivity (Main Area) | Residual DNA Positivity Adjacent Low Grade Component* (CIN I or HPV areas) | Nuclease Resistant DNA Positivity by Histologic Diagnosis** |
|---|---|---|---|
| Carcinoma (17) | 0 | 1 out of 4 cases (25%) | 0 out of 17 (0) |
| CIN III (15) | 0 | 4 out of 7 (57%) | 0 out of 15 (0) |
| CIN II (15) | 0 | 4 out of 12 (33%) | 0 out of 15 (0) |
| CIN I (15) | 7 | 7 out of 7 (100%) HPV areas only | 12 out of 15§ (80%) |
| Condyloma (16) | 13 | N/A | 13 out of 16 (81%) |

*High grade dysplasias (CIN II & III) and carcinomas may have coexisting adjacent areas with the precursor low grade component (condylomas & CIN I) within the same histological specimen. Analysis of CIN II to cancer cases showed when present in the biopsy specimen, the adjacent lower grade component had a statistically significant decrease in residual DNA positivity, compared to specimens that were actual low grade cases where positivity was about 80%.

**Residual DNA positivity is based upon the staining frequency of the main (predominant) lesion type, except in CIN I cases.

§In CIN I cases, both the CIN I region and the HPV area within a given histological specimen were considered together rather than distinctly. The location of DNA positivity was noted but not distinguished because the natural history and clinical management and low grade cervical lesions are similar. Histopathologically CIN I and condyloma are classified as simply low grade lesions (2, 3).

TABLE 2

Comparison of DNAse Staining With In-Situ Hybridization§

| Histology Cases | DNAse Stain* | In-situ |
|---|---|---|
| Condyloma | ++ | 6/11, 16/18 |
| Condyloma | + | — |
| CIN I | − | 6/11 |
| CIN I | − | — |
| CIN II | − | — |
| CIN II | − | — |
| CIN III | + | 31/33 |
| CIN III | − | — |
| Cancer | − | — |
| Cancer | − | — |

§Two cases had homologous areas staining with both methods. DNAse staining did not appear to be HPV type specific.
*DNAse staining of low grade areas for each case

TABLE 3

Oncogenic Human Papillomvirus (+) patients that had complete regression

| Surveillance | Regression Patient* | | | | | | | | | |
|---|---|---|---|---|---|---|---|---|---|---|
| | 1 | 2 | 3 | 4 | 5 | 6 | 7 | 8 | 9 | 10 |
| Nuclease Resistant DNA Status | + | + | + | − | + | + | − | + | + | + |
| 1 Year Follow-up Biopsy | HPV | Neg | Neg | Neg | HPV | Neg | HPV | Neg | HPV | Neg |
| 2 Year Follow-up Biopsy | Neg | x | x | x | Neg | x | Neg | x | Neg | x |
| Total Number of paps | 5 | 3 | 3 | 3 | 5 | 3 | 5 | 3 | 5 | 3 |

*Eighty percent (2/10) of HPV (+) patients that had complete regression of their infection had their initial HPV biopsy positive for residual DNA staining.

TABLE 4

Oncogenic Human Papillomvirus (+) patients that progressed to high grade lesions

| Surveillance | Progression Patients* | | | | | | | |
|---|---|---|---|---|---|---|---|---|
| | 1 | 2 | 3 | 4 | 5 | 6 | 7 | 8 |
| Nuclease Resistant DNA Status | + | − | − | − | + | − | − | − |
| 1 Year Follow-up Biopsy | HPV | CIS | CIN-II | HPV | HPV | CIN-II | CIN-II | HPV |
| 2 Year Follow-up Biopsy | CIN-II | x | x | CIN-II | x | x | x | CINII |
| Number of paps | 5 | 3 | 3 | 5 | 3 | 3 | 3 | 5 |

CIS—carcinoma in-situ,
*Seventy-five percent (6/8) of HPV (+) patients that progressed to high grade dysplasia had their initial HPV biopsy negative for residual DNA staining.

REFERENCES

1. Landis et al., Cancer statistics, 1999. *CA Cancer J Clin* 1999; 49(1):8-31
2. Wright et al., Precancerous lesions of the cervix. In: Kurman R J, ed. *Blausteins pathology of the female genital tract*. 5th ed. New York: Springer; 2002:253-324.
3. Well, Human papillomavirus associated lesions of the lower female genital tract. In: lowe D, Fox H, Editors. Advances in Gynacological Pathology. UK: Churchill Livingstone, 1992: 79-97
4. Syrjänen, Spontaneous evolution of intraepithelial lesions according to the grade and type of the implicated human papillomavirus (HPV). *Eur J Obstet Gynecol Reprod Biol* 1996; 65(1):45-53
5. Hines et al., Human Papillomaviruses: Their clinical significance in the management of cervical carcinoma. Oncology 1995; 9:279-85
6. Solomon et al., Cervical cancer screening rates in the United States and the potential impact of implementation of screening guidelines. *CA Cancer J Clin* 2007; 57(2): 105-11
7. Ostör, Natural history of cervical intraepithelial neoplasia: a critical review. *Int J Gynecol Pathol* 1993; 12(2): 186-92
8. Thomison et al., Human papillomavirus: molecular and cytologic/histologic aspects related to cervical intraepithelial neoplasia and carcinoma. Hum Pathol. 2008; 39(2): 154-66.
9. Jones H W 3$^{rd}$. Impact of the Bethesda System. *Cancer* 1995; 76(10 Suppl):1914-1918
10. Jones and Davey, Quality management in gynecologic cytology using interlaboratory comparison. *Arch Pathol Lab Med* 2000; 124(5):672-81
11. Spitzer, Screening and management of women and girls with human papillomavirus infection. Gynecol Oncol 2007; 107(2 Suppl):S14-8
12. Wright et al., 2006 American Society for Colposcopy and Cervical Pathology-sponsored Consensus Conference. 2006 consensus guidelines for the management of women with cervical intraepithelial neoplasia or adenocarcinoma in situ. Am J Obstet Gynecol 2007; 197(4):340-5.
13. Wright et al., 2006 American Society for Colposcopy and Cervical Pathology-sponsored Consensus Conference. 2006 consensus guidelines for the management of women with cervical intraepithelial neoplasia or adenocarcinoma in situ. *J Low Genit Tract Dis* 2007; 11(4):223-39.
14. Guido et al., ASCUS LSIL Triage Study (ALTS) Group. Postcolposcopy management strategies for women referred with low-grade squamous intraepithelial lesions or human papillomavirus DNA-positive atypical squamous cells of undetermined significance: a two-year prospective study. *Am J Obstet Gynecol* 2003; 188(6):1401-5
15. Cox et al., ASCUS-LSIL Triage Study (ALTS) Group. Prospective follow-up suggests similar risk of subsequent cervical intraepithelial neoplasia grade 2 or 3 among women with cervical intraepithelial neoplasia grade 1 or negative colposcopy and directed biopsy. *Am J Obstet Gynecol* 2003; 188(6):1406-12.

16. Belinson et al., Shanxi Province Cervical Cancer Screening Study: a cross-sectional comparative trial of multiple techniques to detect cervical neoplasia. *Gynecol Oncol* 2001; 83(2):439-44

17. Jakobsson et al., Preterm delivery after surgical treatment for cervical intraepithelial neoplasia. *Obstet Gynecol* 2007; 109:309-13.

18. Sadler et al., Treatment for cervical intraepithelial neoplasia and risk of preterm delivery. *JAMA* 2004; 291(17): 2100-6.

19. Bruinsma et al., Precancerous changes in the cervix and risk of subsequent preterm birth. BJOG 2007; 114(1):70-80.

20. de Oliveira et al., Prediction of high-grade cervical disease with human papillomavirus detection in women with glandular and squamous cytologic abnormalities. *Int J Gynecol Cancer* 2006; 16(3):1055-62

21. Schiffman and Solomon, Findings to date from the ASCUS-LSIL Triage Study (ALTS). *Arch Pathol Lab Med* 2003; 127(8):946-9

22. Wells, Human papillomavirus associated lesions of the lower female genital tract. In: lowe D, Fox H, Editors. Advances in Gynacological Pathology. UK: Churchill Livingstone, 1992: 79-97.

23. Yoshida et al., Quantitative real-time polymerase chain reaction analysis of the type distribution, viral load, and physical status of human papillomavirus in liquid-based cytology samples from cervical lesions. *Int J Gynecol Cancer* 2008; 18(1):121-7

24. Jeon and Lambert, Integration of human papillomavirus type 16 DNA into the human genome leads to increased stability of E6 and E7 mRNAs: implications for cervical carcinogenesis. *Proc Natl Acad Sci USA* 1995; 92(5):1654-8

25. Park et al., Physical status and expression of HPV genes in cervical cancers. *Gynecol Oncol* 1997; 65(1):121-9

26. Lucia et al., A histochemical method for demonstrating papilloma virus infection in paraffin-embedded tissue. *Am J Clin Pathol* 1984; 82(5):589-93

27. Chacho et al., Influence of human papillomavirus on DNA ploidy determination in genital condylomas. Cancer 1990; 65: 2291-94

28. William, Histochemical observation of Verruca vulgaris. J Invest Dermatol 1961; 37: 279-82

29. Syrjänen et al., Electron microscopy in assessment of the biological behavior of human papillomavirus infections in the uterine cervix. *Neoplasma* 1986; 33(4):493-505.

30. Syrjänen et al., Electron microscopic assessment of cervical punch biopsies in women followed-up for human papillomavirus (HPV) lesions. *Arch Geschwulstforsch* 1985; 55(2):131-8

31. Bacus and Grace, Optical microscope system for standardized cell measurements and analyses. Appl. Optics 1987; 26:3280-93

32. Ceballos et al., Reproducibility of the histological diagnosis of cervical dysplasia among pathologists from 4 continents. *Int J Gynecol Pathol* 2008; 27(1):101-7

33. Malpica et al., Kappa statistics to measure interrater and intrarater agreement for 1790 cervical biopsy specimens among twelve pathologists: qualitative histopathologic analysis and methodologic issues. Gynecol Oncol 2005; 99(3 Suppl 1):S38-S52

34. Creagh et al., Pathologist variation in reporting cervical borderline epithelial abnormalities and cervical intraepithelial neoplasia. *J Clin Pathol* 1995; 48(1):59-60

35. Wright et al., 2006 American Society for Colposcopy and Cervical Pathology-sponsored Consensus Conference. 2006 consensus guidelines for the management of women with abnormal cervical cancer screening tests. *Am J Obstet Gynecol* 2007; 197(4):346-55

36. ASCUS-LSIL Triage Study (ALTS) Group. A randomized trial on the management of low-grade squamous intraepithelial lesion cytology interpretations. *Am J Obstet Gynecol* 2003; 188(6):1393-400

37. Saslow et al., American Cancer Society Guideline for the Early Detection of Cervical Neoplasia and Cancer. *J Low Genit Tract Dis* 2003; 7(2):67-86

38. Monk and Tewari, The spectrum and clinical sequelae of human papillomavirus infection. *Gynecol Oncol* 2007; 107(2 Suppl 1):56-13

39. Zur Hausen, Papillomaviruses causing cancer: evasion from host-cell control in early events in carcinogenesis. *J Natl Cancer Inst* 2000; 92(9):690-8.

40. Münger, The role of human papillomaviruses in human cancers. Front Biosci 2002; 7:d641-9.

41. Pingoud A M, editor. Restriction endonucleases. Berlin; New York: Springer; 2004.

42. REBASE: The Restriction Enzyme Database [database online] New England Biolabs. Available at: http://rebase.neb.com/rebase/rebase.serv.html. Accessed Jun. 11, 2008.

43. Roberts R J, Macelis D. REBASE—restriction enzymes and methylases. *Nucleic Acids Res* 1996; 24(1):223-35

44. Furusawa and Cutting, Detection of viral DNA in the inclusion bodies of ectromelia-infected tumor cells with fluorescence microscopy. *Virology* 1960; 11:632-4

45. Schulte, Hematoxylin and the Feulgen Reagent in Nuclear staining. In: Boon M L, KOK L P, editors. Standardization and quantitation of diagnostic staining in cytology Leiden Columbo Press, 1986: 15-26

What is claimed is:

1. A method of distinguishing benign human papilloma virus (HPV) infection from the presence of at least one malignant lesion in HPV-infected tissue in a subject, comprising the steps of:
   (a) obtaining at least one tissue sample from the subject;
   (b) digesting the sample with endonuclease; and
   (c) staining the sample for the presence of endonuclease-resistant DNA, wherein presence of said DNA indicates benign HPV infection and a disease caused by HPV would regress, wherein absence of endonuclease-resistant DNA indicates the presence of at least one malignant lesion in the tissue of the subject and a disease caused by HPV would progress.

2. The method of claim 1, wherein the endonuclease is selected from the group consisting of DNAse I, DNAse II alpha, DNAse II beta, an endodeoxyribonuclease, and genetically engineered endonucleases.

3. The method of claim 1, wherein the samples comprise paraffin-embedded tissue blocks.

4. The method of claim 1, wherein endonuclease-resistant DNA staining is performed by a method selected from the group consisting of Feulgen staining, thionin staining, gallocyanin chromalum nuclear staining, Cuprolinic Blue staining, fluorescence DNA staining, hematoxylin staining, antibody DNA staining, DNA staining using a molecular probe, and any variant or combination thereof.

5. The method of claim 1, wherein counterstaining is performed on the samples to improve detection of abnormal cells.

6. The method of claim 5, wherein the counterstaining is performed by using antibodies, DNA probes or RNA probes that bind to HPV components or tumor antigens or antigens of dedifferentiation.

7. The method of claim 1, wherein the tissue samples are selected from the group consisting of lung tissue samples, oral tissue samples, vulvar tissue samples, penile tissue samples, anal tissue samples, cervical tissue samples, and skin samples.

8. The method of claim 7, wherein presence of endonuclease-resistant DNA in the cervical samples indicates benign HPV infection or low grade dysplasia (cervical intraepithelial neoplasia grade I), wherein absence of endonuclease-resistant DNA in the cervical samples indicates high grade dysplasia (cervical intraepithelial neoplasia grade II or grade III) or cancer.

\* \* \* \* \*